(12) United States Patent
Biechele et al.

(10) Patent No.: US 8,489,362 B2
(45) Date of Patent: Jul. 16, 2013

(54) METHOD FOR DETERMINING FAILURE RATE OF AN ELECTROCHEMICAL SENSOR

(75) Inventors: Peter Biechele, Freiburg (DE); Thilo Trapp, Waldheim (DE); Martin Freudenberger, Schwaikheim (DE); Jorg-Martin Muller, Stuttgart (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 315 days.

(21) Appl. No.: 12/959,937

(22) Filed: Dec. 3, 2010

(65) Prior Publication Data
US 2011/0191063 A1    Aug. 4, 2011

(30) Foreign Application Priority Data
Dec. 4, 2009    (DE) .......................... 10 2009 047 550

(51) Int. Cl.
*G06F 15/00*    (2006.01)
(52) U.S. Cl.
USPC .......................................................... 702/183

(58) Field of Classification Search
USPC .................................................. 702/182, 183
See application file for complete search history.

(56) References Cited

U.S. PATENT DOCUMENTS
7,581,434 B1 *    9/2009    Discenzo et al. ............ 73/53.01

FOREIGN PATENT DOCUMENTS
DE    10 2004 063 496 B4    7/2006
DE    10 2005 048 969 A1    5/2007
DE    10 2008 051 653 A1    8/2009

* cited by examiner

*Primary Examiner* — Bryan Bui
(74) *Attorney, Agent, or Firm* — Bacon & Thomas, PLLC

(57) ABSTRACT

A method for determining a failure rate of an electrochemical sensor type for a process, wherein the process is defined by determined values, or value intervals, of a plurality of specified process parameters, and wherein a plurality of defect types is specified for the sensor type, comprising steps as follows: assigning, by means of expert knowledge, a defect rate to each combination of one of the values, or value intervals, of the specified process parameters and one of the specified defect types; and calculating the failure rate of the sensor type according to a calculational specification with application of the defect rates assigned to the combinations of a value, or value interval, of a process parameter and a defect type.

10 Claims, 6 Drawing Sheets

Fig. 2 a) Waste Water:

|     | Para $_1$ | Para $_2$ | ... | Para $_j$ | ... |
|-----|-----------|-----------|-----|-----------|-----|
| D $_1$ | R $_{11}$ | R $_{12}$ | ... | R $_{1j}$ | ... |
| D $_2$ | R $_{21}$ | R $_{22}$ | ... | R $_{2j}$ | ... |
| ⋮   | ⋮         | ⋮         | ... | ⋮         | ... |
| D $_i$ | R $_{i1}$ | R $_{i2}$ | ... | R $_{ij}$ | ... |
| ⋮   | ⋮         | ⋮         | ... | ⋮         | ... | b) Waste Water:

|     | Para $_1$ | Para $_2$ | ... | Para $_j$ | ... |
|-----|-----------|-----------|-----|-----------|-----|
| D $_1$ | P $_1$ | P $_2$ | ... | P $_0$ | ... |
| D $_2$ | P $_0$ | P $_4$ | ... | P $_1$ | ... |
| ⋮   | ⋮     | ⋮     | ... | ⋮     | ... |
| D $_i$ | P $_2$ | P $_1$ | ... | P $_3$ | ... |
| ⋮   | ⋮     | ⋮     | ... | ⋮     | ... |

Fig. 2 c) Waste Water (Example):

|  | pH-Value 6-9 | Pressure 900-1100 mbar |
|---|---|---|
| Glass membrane cracked | $10^{-10}$ 1/h | $10^{-8}$ 1/h |
| Diaphragm blocked | $10^{-10}$ 1/h | $10^{-10}$ 1/h |

Fig. 3 a) Dairy:

|  | Para$_1$' | Para$_2$' | ... | Para$_j$' | ... |
|---|---|---|---|---|---|
| D$_1$ | R$_{11}$' | R$_{12}$' | ... | R$_{1j}$' | ... |
| D$_2$ | R$_{21}$' | R$_{22}$' | ... | R$_{2j}$' | ... |
| ⋮ | ⋮ | ⋮ | ⋮ | ⋮ | ... |
| D$_i$ | R$_{i1}$' | R$_{i2}$' | ... | R$_{ij}$' | ... |
| ⋮ | ⋮ | ⋮ | ⋮ | ⋮ | ... | b) Dairy:

|  | Para$_1$' | Para$_2$' | ... | Para$_j$' | ... |
|---|---|---|---|---|---|
| D$_1$ | 0 | 2 | ... | 0 | ... |
| D$_2$ | 3 | 1 | ... | 1 | ... |
| ... | ... | ... | ... | ... | ... |
| D$_i$ | 0 | 0 | ... | 0 | ... |
| ⋮ | ... | ... | ... | ... | ... |

Fig. 3 c) Dairy:

|  | Para $_1$' | Para $_2$' | ... | Para $_j$' | ... |
|---|---|---|---|---|---|
| D $_1$ | P $_0$' | P $_2$' | ... | P $_0$' | ... |
| D $_2$ | P $_3$' | P $_1$' | ... | P $_1$' | ... |
| ⋮ | ... | ... | ... | ... | ... |
| D $_i$ | P $_0$' | P $_0$' | ... | P $_0$' | ... |
| ... | ... | ... | ... | ... | ... | d) Dairy:

|  | Para $_1$' | Para $_2$' | ... | Para $_j$' | ... |
|---|---|---|---|---|---|
| D $_1$ | P | 100 P | ... | P | ... |
| D $_2$ | 1000 P | 10 P | ... | 10 P | ... |
| ⋮ | ... | ... | ... | ... | ... |
| D $_i$ | P | P | ... | P | ... |
| ... | ... | ... | ... | ... | ... |

Fig. 3 e) Waste Water:

|  | Para$_1$ | Para$_2$ | ... | Para$_j$ | ... |
|---|---|---|---|---|---|
| D$_1$ | 1 | 2 | ... | 0 | ... |
| D$_2$ | 0 | 4 | ... | 1 | ... |
| ⋮ | ⋮ | ⋮ | ⋮ | ⋮ | ... |
| D$_i$ | 2 | 1 | ... | 3 | ... |
| ⋮ | ⋮ | ⋮ | ⋮ | ⋮ | ... | f) Waste Water:

|  | Para$_1$ | Para$_2$ | ... | Para$_j$ | ... |
|---|---|---|---|---|---|
| D$_1$ | 10P | 100P | ... | P | ... |
| D$_2$ | P | 10000P | ... | 10P | ... |
| ⋮ | ⋮ | ⋮ | ⋮ | ⋮ | ... |
| D$_i$ | 100P | 10P | ... | 1000P | ... |
| ⋮ | ⋮ | ⋮ | ⋮ | ⋮ | ... |

METHOD FOR DETERMINING FAILURE RATE OF AN ELECTROCHEMICAL SENSOR

TECHNICAL FIELD

The invention relates to a method for determining a failure rate of an electrochemical sensor type, for application in a predetermined process for measuring a process variable of a process medium.

BACKGROUND DISCUSSION

In many applications, e.g. of measuring systems with sensors in process measurements technology, especially for determining a measured variable of a process medium, it is desirable to know a failure rate of the measuring systems and to take such into consideration for safety purposes. International standard IEC 61508 gives a method, according to which a failure rate of the total measuring system can be ascertained on the basis of failure rates of individual portions of a measuring system. Among other things, from the ascertained failure rate, there results according to this standard a classification of the measuring system in terms of a Safety Integrity Level, or SIL.

Measuring systems in process measurements technology, especially in the wastewater, drinking water, pharmaceuticals, chemistry and food technology fields, comprise, besides electronic and mechanical components, frequently also electrochemical sensor elements, which often work according to a potentiometric or amperometric measuring principle. Examples of potentiometric sensor types are ion-selective electrodes, of which the most known representative is the glass electrode for pH-value measurement. These sensor types have a measuring half cell and a reference half-cell. The measuring half cell includes an ion-selective membrane, in the case of the pH-glass electrode a glass membrane, which is in contact with the process medium and at which an electrochemical potential forms. The electrochemical potential on the membrane is correlated with the concentration of the ions to be detected, for example, in the case of a pH-glass electrode, $H_3O^+$-ions. The potential formed on the membrane is measured against a reference electrode providing a stable reference potential, for example, an Ag/AgCl-electrode, which is in contact with the process medium via a diaphragm.

An example of an amperometric sensor type is a dissolved oxygen sensor according to the principle of the Clark-electrode. This sensor type includes an electrolyte filled measuring chamber, which contains a working- and at least one counterelectrode, and which is isolated from the process medium by means of a membrane permeable for the analyte, e.g. oxygen dissolved in the medium. Analyte diffusing through the membrane is oxidized or reduced on the working electrode, depending on whether the working electrode is connected as anode or cathode. The chemical conversion of the analyte on the working electrode effects an electrical current flow, which is correlated with the analyte concentration in the process medium.

Failure rate is defined as probability of failure referenced to a certain time interval, e.g. probability of failure per hour, or PFH, for short. Failure rates of electronic components are calculatable, or at least estimatable, with the assistance of known tables for most components of a measuring system. Likewise there are, for mechanical components, methods and manners of proceeding, which make such failure rates accessible. In the case of electrical and mechanical components, it is most often known, how the failure rate changes in the case of varying environmental conditions. For example, the change of failure rates of such components with temperature changes can be described on the basis of the Arrhenius equation. Since electronic and mechanical components also, most often, are not directly in contact with the medium, as a rule, only the environmental conditions described by temperature, pressure, humidity and electromagnetic disturbances and oscillations/vibrations are to be noted as influencing variables for the failure rate.

Very much more difficult, however, is the situation in the case of appraisal of electrochemical sensor types, especially in the case of amperometric or potentiometric, sensor types. The process parameters of the process, in which sensor elements of these sensor types are applied, have a strong influence on the life of the sensor elements and therewith also on the probability of failure, or the failure rate, of the corresponding sensor type.

Since the process parameters of the process significantly influence the probability of failure of a sensor element of a determined electrochemical sensor type, a uniform failure rate, i.e. a failure rate unified for all possible processes, such as is given in the case of electronic or mechanical system components, would be of only smaller meaning for an electrochemical sensor element of the specified sensor type. Because of the multitude of conceivable processes, in which sensor elements of one and the same sensor type can be applied, it is, however, also impractical, to determine for each of these processes its own failure rate on the basis of experiments.

SUMMARY OF THE INVENTION

An object of the invention, therefore, is to provide a method for determining a failure rate of an electrochemical sensor type for a predetermined process. Especially, the method should permit not only determining a failure rate referenced to a single or to a number of similar processes, but, instead enable the determining of failure rates for any processes, which have very different process parameters and correspondingly load a sensor element of the sensor type in significantly different measure.

This object is achieved by a method for determining a failure rate of an electrochemical sensor type for a process, wherein the process is defined by certain values, or value intervals, especially predetermined, values, or value intervals, of a plurality of predetermined process parameters, and wherein a plurality of error types is specified for the sensor type, comprising steps as follows:
  assigning, by means of expert knowledge, a defect rate to each combination of one of the values, or value intervals, of the predetermined process parameters and one of the predetermined defect types; and
  calculating the failure rate of the sensor type according to a calculational specification with application of the defect rates assigned to the combinations of a value, or value interval, of a process parameter and a defect type.

A process, for the purposes of the herein described method, is defined by a plurality of process parameters, such as, for example, temperature, pressure, pH-value, flow velocity of the process medium, concentration of aggressive media, such as e.g. hydrofluoric acid (HD), sodium hydroxide or sulfur compounds, oscillation frequency, or oscillation amplitude, of the sensor relative to the medium at the measuring point, the concentration of solids in the medium, pressure-, temperature- and/or pH-value changes, the concentration of organic solvent in the medium. In given cases, also an encompassing parameter can be specified, which reflects synergistic effects in the case of combination of the individual process parameters. Preferably, such process parameters are considered and/or defined, which influence the life, or the probability of failure, of the considered sensor type.

A certain process is determined by certain values or value intervals of such process parameters, e.g. a food technology process can be determined by a pH-value between 9 and 13, a temperature between 20 and 70° C., a pressure of 1000 mbar, etc.

The process and its influence on the failure rate of a sensor element of a certain sensor type in this method is broken down into individual combinations of predetermined values or value intervals of the process parameters and possible kinds of defects of the sensor type. Defect types can be, for example, certain kinds of damage of the sensor membrane, such as e.g. crack, abrasion or chemical contamination. Defect types can also concern defects occurring at the diaphragm of a reference electrode, such as e.g. blocking or mechanical destruction.

By means of expert knowledge, thus, a defect rate can be assigned to each individual combination of a value or value interval of a process parameter and a defect type. These defect rates, which result from consideration of the influence of an individual process parameter on an individual defect type of the sensor type, can by means of a predetermined calculational specification be converted to a probability of failure of the sensor type.

The calculational specification comprise can the forming of the sum of the defect rates assigned to all combinations of a value or value interval of a process parameter and a defect type.

If, for example, n defect types $D_1, D_2, D_i, \ldots D_n$ are specified and the process is defined via values or value ranges $Para_1, Para_2, \ldots Para_j, Para_m$ of m process parameters, then the sum S of the defect rates $R_{ij}$ assigned to all combinations of a value or value interval of a process parameter and a defect type can be expressed as $$S = \sum_{i=1}^{n} \sum_{j=1}^{m} R_{ij},$$

wherein $R_{ij}$ is a defect rate, which is assigned to the combination of the defect type $D_i$ with the value, or value interval, $Para_j$ of the process parameter.

In the simplest case, the failure rate of the sensor type is obtained by forming the sum S, i.e. by simple summing of all defect rates $R_{ij}$. It is also possible to multiply individual or all defect rates $R_{ij}$ of the sum with a weighting factor, in order to emphasize more strongly the influence of especially important or safety-relevant combinations of a value, or value interval of a process parameter and a defect type.

The plurality of defect types for the sensor type can be ascertained, for example, by means of a qualitative failure mode and effects analysis, FMEA, for short).

Besides the process parameters of the actual process, which have an influence on the probability of failure, or the failure rate of the considered sensor type, also influences of maintenance measures on the failure rate can be heeded. Such maintenance measures can be, for example, regular calibrations, cleanings or sterilizations. Also the frequency, with which such maintenance measures are performed, influences the failure rate of an electrochemical sensor type significantly. There are different options for taking the influence of maintenance measures into consideration in the method described here for determining the failure rate of an electrochemical sensor type. For example, an option is to take the type and frequency of maintenance measures into consideration when specifying the values or value ranges of the process parameters. If, for example, there are between the process cycles of the considered process regularly cleaning steps at extreme pH-values and temperatures, this can be taken into consideration by specifying a broader value range of the process parameter "pH-value" and the process parameter "temperature". Another opportunity is to take the influence of maintenance measures on the failure rate into consideration in the form of one or a plurality of supplementally specified, defect types. In the case of a third variant, the expert can take the additional influence of maintenance measures into consideration in the associating of the defect rates to the individual combinations of value or value range of the process parameters and defect type.

The step of assigning a defect rate to each combination of, in each case, one of the values or value intervals of the specified process parameters and, in each case, one of the specified defect types can comprise substeps as follows:

Specifying a limited number of qualitative defect rate classes, which, in each case, represent different probabilities of occurrence of a defect type within one and the same time interval;

assigning, in each case, one of the qualitative defect rate classes to each combination of a value or value interval of a process parameter and a defect type by means of expert knowledge; and replacing the assigned qualitative defect rate classes, in each case, with a defect rate value.

This procedure permits, for example, by an expert, a purely qualitative evaluation of the influence of the, in each case, considered specified value or value interval of a process parameter on the occurrence the, in each case, considered defect type. The assigning by means of expert knowledge can occur by a subjective expert estimate. It is also possible to provide an expert knowledge-database, in which a large number of expert-estimates are stored for a large number of process parameter/defect type-combinations. In this case, the step of assigning, in each case, of one of the qualitative defect rate classes to each combination of a value or value interval and a defect type of a process parameter and a defect type can be performed by means of a data processing installation with access to the expert knowledge-database.

Advantageously, the number of specified defect rate classes lies between two and ten.

The qualitative defect rate classes can be represented, for example, by increasing whole numbers, such as 0 to 4, wherein the higher number, in each case, represents a higher defect rate. Thus, the number "0" can represent the qualitative defect rate class "arises essentially never", the number "1" the qualitative defect rate class "arises very seldom", the number "2" the defect rate class "arises seldom", the number "3" the defect rate class "arises frequently" and the number "4" the defect rate class "arises very frequently".

The defect rate classes and the corresponding defect rate values are preferably so specified, that they represent, in each case, probabilities of occurrence of a defect type within one and the same time interval differing from one another by at least one order of magnitude. Thus, the defect rate value to be assigned to the defect rate class "arises very seldom" is at least one order of magnitude higher than the defect rate value assigned to the defect rate class "arises essentially never". Correspondingly, the defect rate value assigned to the defect rate class "arises seldom" is, in turn, at least one order of magnitude higher than the defect rate value assigned to the defect rate class "arises very seldom", etc.

The assigning of defect rates to combinations of values or value ranges of the process parameters and defect types occurs in this method variant thus by assigning the specified defect rate values corresponding to the classes.

In an alternative method variant, the step of assigning, in each case, a defect rate to each combination of, in each case, one of the values or value intervals of the specified process parameters and, in each case, one of the specified defect types includes substeps as follows:

Specifying a limited number of defect rate values, which represent, in each case, different probabilities of occurrence of a defect type within one and the same time interval; and assigning, in each case, one of the defect rate values to each combination of a value or value interval of a process parameter and a defect type by means of expert knowledge.

Advantageously, the number of the specified defect rate values lies between two and ten. Also in the case of this method variant, it is advantageous, when the different defect rate values, in each case, differ from one another by at least one order of magnitude.

Also in this method variant, there occurs, thus, the assigning of defect rates to combinations of values or value ranges of the process parameters and defect types by assigning individual, specified defect rate values.

Of course, it is also possible to specify for the expert no fixed defect rate values, but, instead, to let the expert assign freely selectably defect rates $R_{ij}$ to the individual combinations of values, or value ranges of the process parameters and defect types.

In the assigning of defect rates, e.g. by assigning specified defect rate values to the combinations of values or value intervals of process parameters and defect types, the person skilled in the art can simultaneously take into consideration the additional process parameter values, or value intervals. This has the advantage that a conservative result is obtained for the failure rate, since the probability theoretical dependencies are also taken into consideration. For example, the person skilled in the art can, in assigning a defect rate value to a combination of the defect type "crack in the measuring membrane" and a specified pH-value range as process parameter value interval, also take into consideration the influence of the pressure value range specified for the process by assigning the defect rate in such a manner that synergistic effects of pressure and pH-value in reference to the sensor failure rate are taken into consideration. This leads to a more exact, conservative result for the failure rate.

The defect rate values to be assigned to the defect rate classes, or the defect rate values assigned in the second method variant directly to the combinations of a value or value interval of a process parameter and a defect type, can be estimated, especially based on expert knowledge.

Alternatively, the defect rate values can be ascertained by means of at least one experiment based on at least one reference process. Preferably, the defect rate values are ascertained based on a plurality of different reference processes.

For experimental ascertaining of the defect rate values, for example, at least one reference process can be specified, which is defined by certain reference process values or reference process value intervals of the plurality of process parameters, and, furthermore, at least the following steps can be performed:

Performing of at least one experiment, in the case of which at least one sensor element the sensor type is loaded according to the determined reference process values or reference process value intervals of the process parameters and ascertaining failure rate of the sensor type in the experiment;

assigning, in each case, one of the qualitative defect rate classes to each combination of a reference process value or reference process value interval of a process parameter and a defect type by means of expert knowledge;

assigning a defect rate value for each qualitative defect rate class by setting in relationship the experimentally ascertained failure rate of the sensor type and the qualitative defect rate classes assigned to the combinations of reference process value or reference process value interval of a process parameter and a defect type, by applying the calculational specification for calculating the failure rate of the sensor type.

To be heeded is that, for ascertaining a failure rate according to the earlier described method for a certain process, the reference process for ascertaining the individual defect rate values must not be defined by the same or similar values or value intervals, as the process, for which the probability of failure of the sensor type is to be ascertained.

Advantageous, however, is when the specified defect types of the sensor type, in the case of ascertaining the defect rates in the reference process, are the same as those, in the case of the determining the probability of failure the sensor type in the case of a determined process differing from the reference process. This especially makes sense, since the defect types are assigned to the sensor type, not, however, to a process. Even though a defect type occurs extremely seldom in a certain process, it should nevertheless be considered.

Also the qualitative defect rate classes in the case of the experimental ascertaining of the defect rate values are the same as those used in the case of determining a probability of failure of the sensor type in the case of an determined process differing from the reference process.

The performed experiment corresponds preferably to the reference process, i.e. it has values or value intervals of the process parameters, which are equal or similar to those of the reference process. Preferably, in such case, the time intervals from the beginning of the experiment up to the failure of the sensor elements are determined for a plurality of sensor elements of the same sensor type. On the basis of the so ascertained time intervals, a failure rate of the sensor elements can be derived. The experiment is preferably executed as an accelerated experiment, in order to obtain a lessening of the experimentation time. This can involve performing the experiment at increased sensor loadings, as compared to the case in the actual reference process. This is then taken into consideration by an acceleration factor. The acceleration factor is the ratio of the degradation of the sensor by the load during the accelerated experiment and the degradation by the load during use in the reference process without accelerated conditions.

The setting in relationship of the experimentally ascertained failure rate of the sensor type and the qualitative defect rate classes assigned to the combinations of reference process value or reference process value interval of a process parameter and a defect type can comprise steps as follows:

assigning a defect rate value to each qualitative defect rate class, wherein the defect rate values are given, in each case, as a function, especially as a multiple, of one and the same unknowns;

inserting the defect rate values as well as the experimentally ascertained failure rate of the sensor type into the calculational specification for calculating the failure rate of the sensor type; and determining the unknowns therefrom.

On the basis of the so ascertained, single unknowns, the defect rate values can be calculated. The defect rate values so derived from the experiment can then be used for ascertaining failure rates of the sensor type in the most varied of processes.

The failure rate of an electrochemical sensor type ascertained according to the above described method can be used for ascertaining a failure rate of a measuring system comprising a sensor element of electrochemical sensor type and a measuring electronics in the context of a failure mode, effects and diagnostics analysis, FMEDA for short), especially in the context of a permit according to the standard IEC 61508. In such case, also the diagnostic means available for the sensor type are to be taken into consideration. These can differ from sensor type to sensor type, depending on technical embodiment.

BRIEF DESCRIPTION OF THE DRAWINGS

The invention will now be described in greater detail on the basis of the appended drawing illustrating an example of an embodiment. The figures of the drawing show as follows:

FIG. 2 is a) a table of defect rates $R_{ij}$ of combinations of defect types $D_i$, and values, or value intervals $Para_j$ of process parameters for a wastewater-process;
  b) the table of a), wherein, as defect rates $R_{ij}$, predetermined defect rate values $P_0$, $P_1$, $P_2$, $P_3$, $P_{P4}$ are assigned to the individual combinations of defect types $D_i$, and values, or value intervals $Para_j$ of process parameters; and
  c) a numerical example for a wastewater process;

FIG. 3 is a) a table of defect rates $R_{ij}'$ of combinations of defect types $D_i$, and values, or value intervals $Para_j'$ of process parameters for a dairy process;
  b) the table of a), wherein, instead of defect rate values $R_{ij}$, qualitative defect rate classes are assigned to the individual combinations of defect types $D_i$, and values, or value intervals $Para_j$ of process parameters;
  c) the table of b), wherein first unknown, experimentally to be determined defect rate values $P_0'$, $P_1'$, $P_2'$, $P_3'$ and $P_4'$ are assigned to the assigned qualitative defect rate classes;
  d) the table of c), wherein the experimentally to be determined defect rate values $P_0'$, $P_1'$, $P_2'$, $P_3'$ and $P_4'$ are expressed as multiples of an unknown P;
  e) a table of individual combinations of defect types $D_i$, and values, or value intervals, $Para_j$ of process parameters for a waste water process corresponding to FIG. 2 a), or b), wherein qualitative defect rate classes are assigned to the individual combinations; and
  f) a table corresponding to the table of e), wherein the defect rate classes are replaced by the defect rate values experimentally ascertained on the basis of the dairy process serving as reference process.

Figure 1:
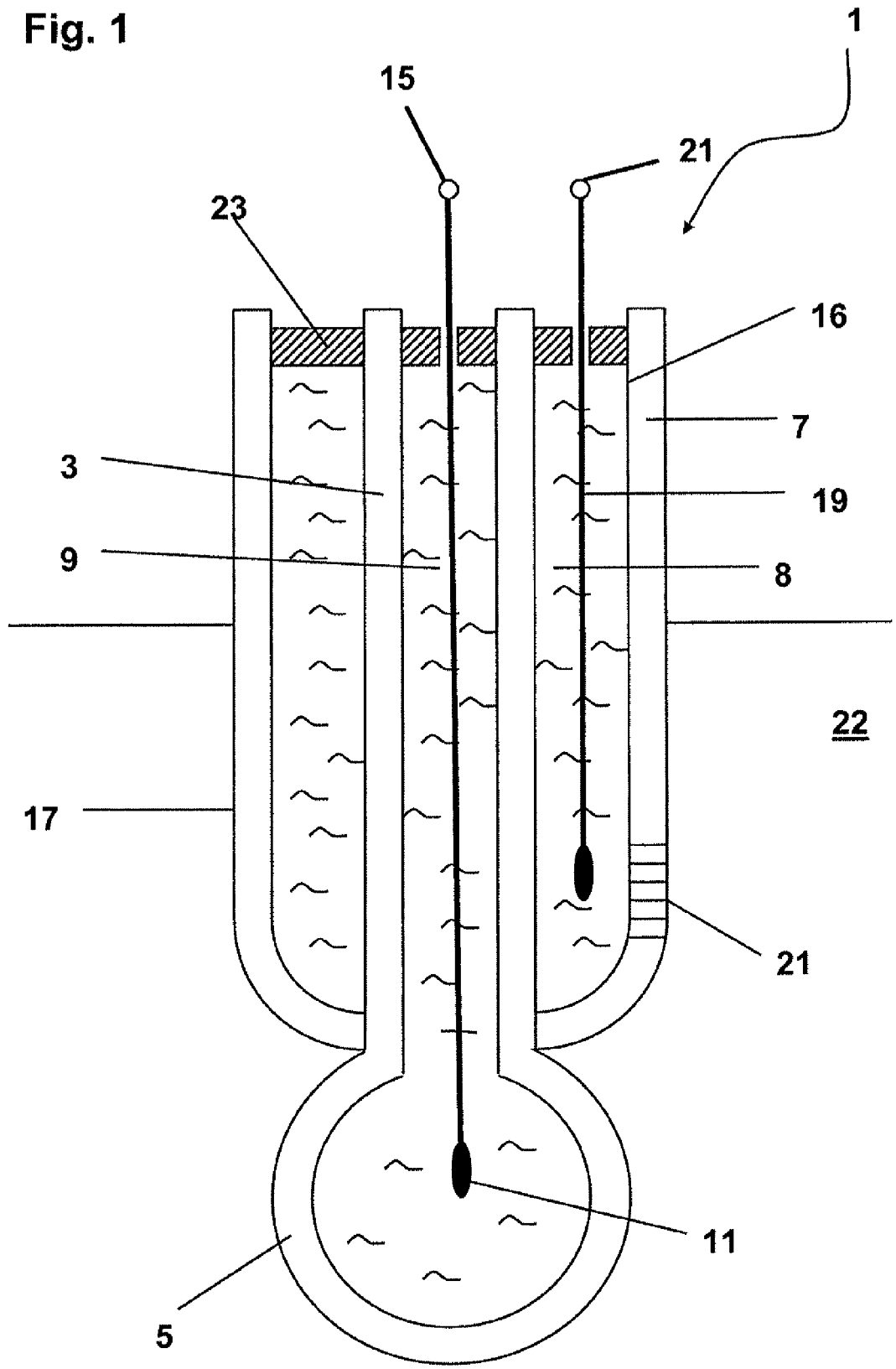
FIG. 1 is a pH-single-rod measuring chain, also referred to as a pH-glass electrode.

DETAILED DISCUSSION IN CONJUNCTION
WITH THE DRAWINGS

FIG. 1 shows first the basic construction of a sensor element 1 of the sensor type represented by a pH-single-rod measuring chain, also referred to as a pH-glass electrode. The sensor element 1 possesses a housing, for example, of glass, which, as a first housing part, has, formed from electrically insulating material, such as e.g. glass or synthetic material, e.g. plastic, an inner tube 3, which is closed terminally by a pH-sensitive, glass membrane 5. The inner tube 3 is surrounded by a second housing part in the form of a tubular sensor shaft 7 formed of electrically insulating, transparent material, such as e.g. glass or a transparent, synthetic material, wherein the tubular sensor shaft 7 is connected in its end region facing the glass membrane 5 with the inner tube 3, so that a ring-shaped inner space 8 is formed extending around the inner tube 3. The ring-shaped inner space 8 is isolated completely sealed to liquid and electrically insulated from the housing interior of the inner tube 3.

The inner space 9 surrounded by the glass membrane 5 and the inner lateral surface of the inner tube 3 is filled with a solution of known pH-value buffering the pH-value, into which extends a potential indicating electrode 11, which is formed, for example, of a chiorided silver wire. The so-formed measuring half cell of the sensor element 1 is connected electrically conductively with a measuring electronics (not shown) via a contact location 15 electrically conductively connected with the potential indicating electrode 11. The potential indicating electrode 11 is, for this, brought through a closure 23, which seals the buffer solution in the measuring half cell.

The inner space 8 surrounded by the housing wall of the inner tube 3 and the inner lateral surface 16 of the tubular sensor shaft 7 is filled with a reference electrolyte, for example, a 3 molar aqueous potassium chloride solution. Extending into the reference electrolyte is a potential indicating electrode 19, which can be formed as the potential indicating electrode 11 by a silver wire coated with silver chloride. Provided In the sensor shaft 7 is a diaphragm 21, which enables an exchange of charge carriers between the inner space bounded by the sensor shaft 7 and the environment. The so formed reference half-cell of the sensor element 1 is connected electrically conductively, via the potential indicating electrode 19 extending through the closure 23, with a contact location 21, which, in turn, serves for connection to the measuring electronics. The measuring electronics includes, among other things, means for determining the potential difference between the potential of the reference half-cell and that of the measuring half cell. It can be accommodated, for example, at least partially, in a plug head located on the end region of the sensor shaft 7 opposite the pH-sensitive glass membrane 5 or in a measurement transmitter connected to the sensor element 1. In measurement operation, the sensor element 1 is immersed with its immersion region, which includes the pH-sensitive glass membrane 5 and a part of the outer lateral surface 17 of the sensor shaft 7, into the measured medium 22.

The probability of failure of the sensor element 1 depends strongly on the kinds of stresses, to which the sensor element 1 is subjected. The stresses are determined by the process, in which the sensor element is applied for measuring a property of a measured medium, e.g. of a process medium. In the case of a pH-single-rod measuring chain, for example, extreme pH-values, such as pH-values between 0 and 1, or between 13 and 14, result in early degradation of the glass membrane 5 and/or the diaphragm 21, and therewith to increasing the probability of failure. Extreme temperatures and pressures, especially also strong fluctuations of temperature and pressure, likewise increase the probability of failure of a pH-single-rod measuring chain.

The method described in the following on the basis of two different examples of embodiments permits ascertaining failure rates of sensor elements of a certain sensor type for any processes, wherein, in the present examples, the sensor type involves a pH-single-rod measuring chain according to FIG. 1. In a first example of an embodiment, the failure rate is ascertained on the basis of estimated defect rates. In a second example of an embodiment, failure rate is determined on the basis of experimentally ascertained defect rates.

1. Example of an Embodiment: Ascertaining Failure Rate on the Basis of Estimated Defect Rates In a first step, defect types of the sensor type, i.e., in the present example, defect types, which can occur in the case of a pH-single-rod measuring chain, and which lead with a certain probability to a defective measuring, or to the failure of the single-rod measuring chain, are specified. These defect types can be determined, for example, by means of a qualitative effects analysis, FMEA. Examples of such defect types in the case of a pH-single-rod measuring chain according to FIG. 1 are cracks, breaking/abrasion, chemical contamination of the glass membrane or deposits on the glass membrane, blocking of the diaphragm by accretion, chemical blocking of the diaphragm, e.g. through precipitation of solids, mechanical destruction of the diaphragm, mechanical destruction of the sensor shaft, and loss of the reference electrolyte or the buffer medium.

In a second step, process parameters are established, with which an arbitrary process, in which the glass electrode can be applied, can be defined, and which, in given cases, can have an influence on the occurrence of the above named, sensor defects. In such case, especially taken into consideration are those parameters which have an influence on the life, or the probability of failure, of the glass electrode. In the case of a glass electrode according to FIG. 1, such parameters are, for example, the pH-value of the process medium, the temperature of the process medium, the pressure, which the sensor element is exposed to, the flow velocity of the process medium, pH-, pressure- and temperature jumps in the course of a process cycle, the concentration of aggressive chemicals, especially of hydrofluoric acid (HF), sodium hydroxide, sulfur compounds, organic solvents, as well as the concentration of solid particles in the measured medium, an oscillation frequency and an oscillation amplitude of the sensor element relative to the measured medium.

In a third step, values or value intervals are ascertained, which the specified process parameters assume in that process, for which a failure rate of the sensor type should be determined. In a typical wastewater process, the pH-value assumes, for example, a value between 6 and 9, the temperature amounts to between 10 and 40° C., the pressure, which the glass electrode is exposed to, lies between 900 and 1100 mbar, the flow velocity of the medium lies between 0 and 1 m/s, etc. Should the failure rate of the sensor type be determined for such a waste water process, the process, "wastewater", is defines by these value intervals of the process parameters: The value interval of the process parameter "pH-value" is thus 6 to 9, the value interval of the process parameter "temperature" 10° C. to 40° C., the value interval of the process parameter "pressure" 900 mbar to 1100 mbar and the value interval of the process parameter "flow velocity" 0 to 1 m/s etc. For defining the process, "wastewater", other process parameters could be specified and, correspondingly, values, or value intervals, of the process parameters defined.

In the case of the establishing the value intervals and/or the defect types, stresses caused by maintenance- and cleaning measures can be taken into consideration. If, for example, there is performed regularly between the process cycles a cleaning cycle, in the case of which the sensor element remains in the process and is likewise cleaned there, e.g. a so called "cleaning in process"-cycle (CIP-cycle), in the case of which extreme pH-values occur, the value interval of the process parameter "pH-value" can be fixed at 0 to 14, in order to take this influence into consideration.

Alternatively, the influence of such cleaning cycles can also be taken into consideration by specifying the value intervals for the process parameters only on the basis of the values arising in the actual process, while the additional influence of the cleaning cycles is taken into consideration by the expert in assigning the defect rates, as will be described below This specification of values or value intervals of process parameters of the investigated process, on the one hand, and defect types of the sensor type, on the other hand, permits a breaking down of the process into individual combinations of process parameter-values, or value intervals, and defect types. In this way, the influence of a process parameter on the occurrence of each defect type can be considered individually.

FIG. 2 a) shows a table, whose rows correspond to individual defect types $D_1, D_2, \ldots D_i, \ldots$ and whose columns are, in each case, assigned to a value, or value interval, $Para_1$, $Para_2$, $Para_j$, ... of a process parameter. Then, to each combination of process parameter value, or value interval, and defect type can be assign its own defect rate $R_{11}, R_{12}, R_{ij}, \ldots$, which produces a contribution to the total failure rate of the sensor element. An expert can estimate a defect rate $R_{ij}$ for each of these combinations. Alternatively, the estimation can also be performed by a data processing installation with access to an expert database.

In order to simplify the assigning of the defect rates $R_{ij}$ to the individual combinations, an option is to specify a limited number of defect rate values, which are assigned to the individual combinations of a value, or value range, $Para_j$ of a process parameter and a defect type $D_i$. For example, five defect rate values $P_0, P_1, P_2, P_3, P_4$ can be specified, which, in each case, differ by at least one order of magnitude, e.g.

| | |
|---|---|
| $P_0$ | $10^{-10}$ 1/h |
| $P_1$ | $10^{-9}$ 1/h |
| $P_2$ | $10^{-8}$ 1/h |
| $P_3$ | $10^{-7}$ 1/h |
| $P_4$ | $10^{-6}$ 1/h |

FIG. 2 b) shows the table of FIG. 2a) modified in that, for each combination of value, or value interval, $Para_j$ of a parameter and a defect type $D_i$, one of the five predetermined defect rate values has been put in place of each defect rate $R_{ij}$.

FIG. 2 c) gives a numerical example for a table for the process, "wastewater". In such case, for the purpose of simplicity, only two possible defect types $D_1, D_2$ are considered for a pH-glass electrode, namely the defect types "glass membrane cracked" and "diaphragm blocked" in the reference half-cell. As process parameters, which have a possible influence on the failure rate of the sensor type, here likewise only two possible process parameters are considered, namely pH-value and pressure, which the sensor element is exposed to in the process. For the pH-value, the value interval $Para_1$ 6 to 9 is given, and for the pressure the value interval $Para_2$ 900 to 1100 mbar. For a pH-glass electrode in a wastewater process, of course, a plurality of further defect types and process parameters can be taken into consideration. For the combination of the value interval 6 to 9 for the pH-value and the defect type "glass membrane cracked", as defect rate the lowest of the predetermined defect rate values, namely $P_0=10^{-10}$ 1/h was assigned. In contrast, for the combination of the value interval 900 to 1100 mbar for the process parameter $Para_2$ "pressure" and the defect type $D_1$ "glass membrane cracked", the defect rate value $P_2=10^{-9}$ 1/h was assigned. The two process parameters "pH-value" and "pressure" have little influence on the second specified defect type $D_2$ "diaphragm blocked", so, for these combinations, the lowest defect rate value $P_0$ was assigned as their defect rates $R_{ij}$.

By a calculational specification, for example, a simple or weighted summing of the defect rates, the failure rate of the sensor type for the considered process, here thus the process, "wastewater", can be calculated from the individual defect rates. In the present example, the failure rate PFH of the sensor type is formed by summing the defect rates $R_{ij}$ assigned for all combinations of a value, or value interval, $Para_j$ of a process parameter and a defect type $D_i$:

$$PFH(wastewater) = \sum_{i=1}^{n} \sum_{j=1}^{m} R_{ij},$$

wherein n is the number of specified defect types and m the number of specified process parameters.

When $N_0$ is the number of instances of $P_0$ in the table illustrated in FIG. 2 b), $N_1$ the number of instances of $P_1$, $N_2$ the number of instances of $P_2$, $N_3$ the number of instances of $P_3$, and $N_4$ the number of instances of $P_4$, the formula for the failure rate reduces to:

$$PFH(wastewater) = \sum_{k=0}^{4} N_k P_k.$$

In the numerical example of FIG. 2 c), the failure rate PFH(wastewater) comes out to PFH(wastewater)=$3P_0+P_2=1.0310^{-8}$.

2. Example of an Embodiment: Ascertaining a Failure Rate on the Basis of Experimentally Ascertained Defect Rates In the case of ascertaining a failure rate on the basis of experimentally ascertained defect rates, one can, basically, proceed in equal manner, as in the earlier described example of an embodiment. However, in this case, the defect rate values $P_0$ to $P_4$ are not estimated, but, instead, defect rate values $P_0'$ to $P_4'$ are derived from experiments.

First, as described for the first example of an embodiment, defect types of the sensor type and process parameters are specified, which exert an influence on the occurrence of the defect types of the sensor type.

For experimental ascertaining of defect rate values, a reference process is specified. As reference process, a typical process can be selected, in which sensor elements of the sensor type to be investigated are frequently applied. For example, as reference process for a pH-glass electrode an in the dairy field applied process can be taken into consideration. For the earlier established process parameters, reference process values, or reference process value intervals, $Para_j$ are specified, which are characteristic for the reference process. In the case of a process from the dairy field (in the following referred to as process, "dairy") with, between the individual process cycles, cleaning steps being performed, in the case of which, in regular cleaning intervals, a cleaning with hot lye and/or hot acid takes place, for the example, the process parameter "pH-value" lies in a value interval between 0 and 14, the process parameter "temperature" has a value interval between 10 and 85° C., and the process parameter "pressure" a value interval between 1000 and 2000 mbar. For additional process parameter, correspondingly, other reference process values, or reference process value intervals, are specified.

Shown in FIG. 3 a) is a table, whose rows correspond to individual defect types $D_1$, $D_2$, ..., $D_i$, ... and whose columns, in each case, are assigned to a reference process value, or reference process value interval, $Para_1'$, $Para_2'$, $Para_j'$, ... of a process parameter. Each combination of process parameter value, or value range, and defect type can then be assign its own defect rate $R_{11}'$, $R_{12}'$, ... $R_{ij}'$, ... which makes a contribution to the total failure rate of the sensor element.

Instead of, as in the previous example of an embodiment, specifying for $R_{ij}$ estimated defect rate values $P_0$ to $P_4$, in the present example of an embodiment, qualitative defect rate classes 0 to 4 are specified, which represent qualitatively different probabilities of occurrence of the individual defect types under the influence of the specified values, or value ranges, of the process parameters:

| | |
|---|---|
| 0 | "arises essentially never" |
| 1 | "arises very seldom" |
| 2 | "arises seldom" |
| 3 | "arises frequently" |
| 4 | "arises very frequently" |

To each combination of values, or value intervals, of the process parameters with defect types of the sensor type, now, by means of expert knowledge, first, in each case, one of these qualitative defect rate classes is assigned. This is shown in FIG. 3 b). To these qualitative defect rate classes, first still unknown defect rate values $P_0'$, $P_1'$, $P_2'$, $P_3'$ and $P_4'$ can be assigned, as shown in FIG. 3 c).

The defect rate values $P_0'$, $P_1'$, $P_2'$, $P_3'$ and $P_4'$ to be assigned to the qualitative defect rate classes are given as functions, especially as multiples, of one and the same unknown P. In this way, a relating of the defect rate values to one another is established. In a simple example, the defect rate values can be given as multiples of an unknown P; compare FIG. 3 d):

$P_0'=P$
$P_1'=10\ P$
$P_2'=100\ P$
$P_3'=1000\ P$
$P_4'=10000\ P$.

In one or more experiments now, the failure rate of a plurality of sensor elements of the sensor type to be examined, in the present example a plurality of pH-glass electrodes, is determined. For this purpose, one or more test runs are performed, in the case of which one or more sensor elements of the considered sensor type are exposed to the specified process conditions of the reference process, i.e. conditions, which correspond to the reference process values, or reference process value intervals, of the considered process parameters. In order to lessen the duration of the experiment, the experiments can also take place with stresses increased over those of the reference process. These increased loadings are taken into consideration by an acceleration factor, in the form of the ratio of the degradation of the sensor by the load during the experiment under increased loadings and the degradation by the load during use in the reference process without these increased loadings. By determining the time span, which passes until the failure of the one or more sensor elements under the experimental conditions, the failure rate PFHexp for the experimental process, in the present example, thus for the process "dairy", i.e. failure rate PFHexp (dairy), of the sensor type, to which the sensor elements belong, can be ascertained. The failure rate PFHexp (dairy) can then be related to the qualitative defect rate classes, or to the defect rate values assigned to these classes.

For this, a specified calculational specification is used, according to which the failure rate PFH results from the individual defect rates of the combinations of values, or value intervals, of the process parameters and the defect types. This calculational recipe is, in the present example of an embodiment, the same as in the first example of an embodiment, namely the summing of the defect rates assigned to all combinations of a value, or value interval, $Para_j$ of a process parameter and a defect type D. When $N_0$ is the number of instances of $P_0'$ in the table illustrated in FIG. 2 b), $N_1$ the number of instances of $P_1'$, $N_2$ the number of instances of $P_2'$, $N_3$ the number of instances of $P_3'$, and $N_4$ the number of instances of $P_4'$, there results the failure rate PFH (dairy) for the dairy process investigated in the experiment:

$$PFH(\text{dairy}) = \sum_{k=0}^{4} N_k P_k'.$$

If one sets the above set forth expressions for the defect rates $P_0'$, $P_1'$, $P_2'$, $P_3'$ and $P_4'$ as multiples of the unknown P and the experimentally determined failure rate PFHexp (dairy) into this equation, the unknown P can be calculated and, from this, in turn, the defect rate values $P_0'$, $P_1'$, $P_2'$, $P_3'$ and $P_4'$ can be calculated.

In this way, thus, the qualitative defect rate classes 0 to 4 assigned to the combinations of reference process value or, value interval, of a process parameter and a defect type are related to the experimentally ascertained failure rate PFHexp of the sensor type, and, from this, the defect rate values $P_0'$, $P_1'$, $P_2'$, $P_3'$ and $P_4'$ can be determined.

With the so ascertained defect rate values $P_0'$, $P_1'$, $P_2'$, $P_3'$ and $P_4'$, now failure rates PFH of the sensor type can be ascertained for any processes. In order to ascertain a failure rate PFH of the sensor type, here thus the failure rate of a pH-glass electrode, for any process, the process is defined by specification of values, or value intervals, of the process parameters. For combinations of defect types of the sensor type with the values, or value intervals, of the process parameters, then, by means of expert knowledge, the qualitative defect rate classes 0 until 4 are assigned, such as described above for the reference process. Here, it makes sense to consider the same process parameters and the same defect types $D_i$, which were used also for the earlier described determining of the defect rate values $P_0'$, $P_1'$, $P_2'$, $P_3'$ and $P_4'$ on the basis of the reference process. Of course, however, other values, or value intervals, can be specified for the process parameters, corresponding to the loadings, which the sensor element experiences in the new process to be examined.

To each combination of defect types with values, or value intervals, of the process parameters, then, corresponding to the defect rate class issued, in each case, for a combination, one of the experimentally ascertained defect rate values $P_0'$, $P_1'$, $P_2'$ $P_3'$, $P_4'$ is assigned. A combination, which was assigned the qualitative defect rate class "0", is thus assigned the defect rate $P_0'=P$, a combination, which was assigned the qualitative defect rate class "1", is assigned the defect rate value $P_1'=10P$, a combination, which was assigned the qualitative defect rate class "2", is assigned the defect rate value $P_2'=100P$, etc.

For example, with the experimentally ascertained defect rate values $P_0'$, $P_1'$, $P_2'$, $P_3'$, and $P_4'$ a failure rate, PFH(wastewater)', can be determined for the sensor type for the waste water process considered in the first example of an embodiment. For this purpose, the expert assigns for the combinations of defect types $D_i$ and values, or value intervals, $Para_s$ shown in the table of FIG. 2 b), instead of the estimated defect rate values $P_0$, $P_1$, $P_2$, $P_3$, $P_4$, first the specified qualitative defect rate classes 0 to 4; compare FIG. 3 e). In a second step, the defect rate classes are replaced with the defect rate values $P_0'$, $P_1'$, $P_2'$, $P_3'$ and $P_4'$ ascertained experimentally on the basis of the dairy process; compare FIG. 3 f).

In order to calculate the failure rate for the new process, the same calculational specification is applied, on the basis of which earlier the experimentally ascertained failure rate PFHexp and the qualitative defect rate classes 0 to 4 were related. In the present example, thus the sum of the defect rate values assigned to all combinations of a value, or value interval, of a process parameter and a defect type is formed:

$$PFH(\text{process}) = \sum_{k=0}^{4} N_k P_k'.$$

wherein $N_k$ is, in each case, the number of combinations, to which the defect rate $P_k$ was assigned.

In the present example, there results, correspondingly, the failure rate of the pH-single-rod measuring chain for the waste water process, PFH(wastewater)':

$$PFH(\text{wastewater}) = \sum_{k=0}^{4} N_k P_k'.$$

In this way, a failure rate PFH of the sensor element can be determined for any desired process.

The failure rates determined in such manner can be used in an FMEDA-method according to the standard IEC 61508 for determining the failure rates of the total sensor system comprising the sensor element 1, the measuring electronics, in given cases, a measurement transmitter for conditioning and output of the signal delivered by the measuring electronics and connecting components for connecting the sensor element with the measuring electronics and the measurement transmitter.

The invention claimed is:

1. A method for determining a failure rate (PFH) of an electrochemical sensor type for a process, wherein the process is defined by determined values, or value intervals, ($Para_j$, $Para_j'$) of a plurality of specified process parameters, and
   wherein a plurality of defect types ($D_i$) is specified for the sensor type, the method comprising the steps:
   assigning, by means of expert knowledge, a defect rate ($R_{ij}$) to each combination of one of the values, or value intervals, ($Para_j$, $Para_j'$) of the specified process parameters and one of the specified defect types ($D_i$); and
   calculating the failure rate (PFH) of the sensor type according to a calculational specification with application of the defect rates ($R_{ij}$) to the combinations of a value, or value interval, ($Para_j$, $Para_j'$) of a process parameter and a defect type ($D_i$).

2. The method as claimed in claim 1, wherein:
   the calculational specification comprises forming the sum of the defect rates ($R_{11}$) assigned to all combinations of a value, or value interval, ($Para_j$, $Para_j'$) of a process parameter and a defect type ($D_i$).

3. The method as claimed in claim 1, wherein:
the plurality of defect types ($D_i$) for the sensor type are specified by means of a failure mode and effects analysis.

4. The method as claimed in claim 1, wherein:
said step of assigning a defect rate ($R_{ij}$) to each combination of one of the values, or value intervals, ($Para_j$, $Para_{ij}'$) of the specified process parameters and one of the specified defect types (Di) comprises the substeps as follows:
specifying a limited number of qualitative defect rate classes, which, in each case, represent different probabilities of occurrence of a defect type ($D_i$) within a time interval;
assigning, by means of expert knowledge, in each case, one of the qualitative defect rate classes to each combination of a value, or value interval, ($Para_j$, $Para_j'$) of a process parameter and a defect type ($D_i$); and
replacing the assigned qualitative defect rate classes, in each case, with a defect rate value ($P_0$, $P_1$, $P_2$, $P_3$, $P_4$; $P_0'$, $P_1'$, $P_2'$, $P_3'$, $P_4'$).

5. The method as claimed in claim 4, wherein:
the defect rate values ($P_0$, $P_1$, $P_2$, $P_3$, $P_4$) are estimated, especially based on expert knowledge.

6. The method as claimed in claim 4, wherein:
the defect rate values ($P_0'$, $P_1'$, $P_2'$, $P_3'$, $P_4'$) are ascertained by means of at least one experiment based on at least one reference process.

7. The method as claimed in claim 6, wherein:
for ascertaining the defect rate values ($P_0'$, $P_1'$, $P_2'$, $P_3'$, $P_4'$), at least one reference process is specified, which is defined by determined reference process values, or reference process value intervals, ($Para_j'$) of the plurality of process parameters; and
furthermore, at least steps are performed as follows:
performing at least one experiment, especially under accelerated conditions, wherein at least one sensor element of the sensor type is loaded according to the ascertained reference process values, or reference process value intervals, ($Para_j'$) of the process parameters and ascertaining a failure rate (PFHexp) of the sensor type in the experiment, especially taking into consideration an acceleration factor when the experiment was performed under accelerated conditions;
assigning, by means of expert knowledge, one of the qualitative defect rate classes to each combination of a reference process value, or reference process value interval, (Park) of a process parameter and a defect type ($D_i$); and
assigning, with application of the calculational specification for calculating the failure rate (PFH) of the sensor type, a defect rate value ($P_0'$, $P_1'$, $P_2'$, $P_3'$, $P_4'$) to each qualitative defect rate class by in relating the experimentally ascertained failure rate (PFHexp) of the sensor type and the qualitative defect rate classes assigned to the combinations of reference process value, or reference process value interval, ($Para_j'$) of a process parameter and a defect type ($D_i$).

8. The method as claimed in claim 7, wherein:
wherein the relating of the experimentally ascertained failure rate (PFHexp) of the sensor type and the qualitative defect rate classes assigned to the combinations of reference process value or reference process value interval ($Par_j'$) of a process parameter and a defect type ($D_i$) comprises the steps as follows:
assigning a defect rate value ($P_0'$, $P_1'$, $P_2'$, $P_3'$, $P_4'$) to each qualitative defect rate class, wherein the defect rate values ($P_0'$, $P_1'$, $P_2'$, $P_3'$, $P_4'$) are given, in each case, as a function of one and the same unknown (P);
inserting the defect rate values ($P_0'$, $P_1'$, $P_2'$, $P_3'$, $P_4'$) as well as the experimentally ascertained failure rate (PFHexp) of the sensor type into the calculational specification for calculating the failure rate (PFH) of the sensor type; and
determining the unknown (P) therefrom.

9. The method as claimed in claim 1, wherein:
said step of assigning a defect rate ($R_{ij}$) to each combination of one of the values, or value intervals, ($Para_j$, $Para_j'$) of the specified process parameters and one of the specified defect types ($D_i$) comprises the substeps as follows:
specifying a limited number of defect rate values ($P_0$, $P_1$, $P_2$, $P_3$, $P_4$; $P_0'$, $P_1'$, $P_2'$, $P_3'$, $P_4'$), which represent, in each case, different probabilities of occurrence of a defect type within a time interval; and
assigning, by means of expert knowledge, in each case, one of the defect rate values ($P_0$, $P_1$, $P_2$, $P_3$, $P_4$; $P_0'$, $P_1'$, $P_2'$, $P_3'$, $P_4'$) to each combination of a value, or value interval, ($Para_j$, $Para_j'$) of a process parameter and a defect type.

10. The use of the failure rate of an electrochemical sensor type ascertained according to a method as claimed in claim 1 ascertaining a failure rate of a measuring system comprising a sensor of electrochemical sensor type and a measuring electronics in the context of a failure mode, effects and diagnostics analysis (FMEDA).

* * * * *